(12) United States Patent
Earle et al.

(10) Patent No.: US 6,939,974 B2
(45) Date of Patent: Sep. 6, 2005

(54) IMIDAZOLE CARBENES

(75) Inventors: John Martyn Earle, Belfast (GB); Richard Kenneth Seddon, Donaghdee (GB)

(73) Assignee: The Queens University of Belfast, Belfast (GB)

( * ) Notice: Subject to any disclaimer, the term of this patent is extended or adjusted under 35 U.S.C. 154(b) by 0 days.

(21) Appl. No.: 10/257,006

(22) PCT Filed: Apr. 5, 2001

(86) PCT No.: PCT/GB01/01487

§ 371 (c)(1),
(2), (4) Date: Feb. 24, 2003

(87) PCT Pub. No.: WO01/77081

PCT Pub. Date: Oct. 18, 2001

(65) Prior Publication Data

US 2003/0186803 A1 Oct. 2, 2003

(30) Foreign Application Priority Data

Apr. 7, 2000 (GB) .............................. 0008707

(51) Int. Cl.⁷ ..................... C07D 233/56; C07D 233/58
(52) U.S. Cl. ................................... 548/347.1
(58) Field of Search ..................... 548/347.1

(56) References Cited

U.S. PATENT DOCUMENTS

| | | | | |
|---|---|---|---|---|
| 5,182,405 A | * | 1/1993 | Arduengo, III | .......... 548/335.1 |
| 5,856,513 A | * | 1/1999 | Ue et al. | .................. 548/347.1 |
| 6,592,988 B1 | * | 7/2003 | Thompson et al. | ......... 428/375 |

FOREIGN PATENT DOCUMENTS

| JP | 2000/003713 A | * | 1/2000 |
|---|---|---|---|
| WO | WO 96 18459 A | | 6/1996 |
| WO | WO 98 27064 A | | 6/1998 |
| WO | WO 01 40146 A | | 6/2001 |

OTHER PUBLICATIONS

Bonhote et al., Inorganic Chemistry, 1996, 35, pp. 1168–1178.*
White et al., CA 90 :204097, 1979.*
Carmichael, Adrian J., et al., "Molecular layering and local order in thin films of 1–alkyl–3–methylimidazolium ionic liquids using x–ray reflectivity" *Mol. Phys.*, 99( 10), 795–800, XP001008042 May (2001).
Carmichael, Adrian J., et al., "Polarity study of some 1–alkyl–3–methylimidazolium ambient–temperature ionic liquids with the solvatochromic dye, Nile Red" *J. Phys. Org. Chem.*, 13(10), 591–595, XP001008060 Oct. (2000).
Hamill, Jennifer T., et al., "Comment on the preparation of the ionic liquid 1–ethyl–3–methylimidazoliu ethanoate: a unique monomeric, homoleptic pentacordinate lead ethanoate complex" *Chem. Commun.* (*Cambridge*) (19), 1929–1930, XP001007296 Sep.–Oct. (2000).
Denk, M. K., et al., "Synthesis and reactivity of subvalent compounds—Part 10. Fast deuterium labeling and the basicity of stable diamino carbenes (imidazole–2–ylidenes)" *Journal of Organometallic Chemistry, Elsevier–Sequoia S.A. Lausanne, CH*, vol. 608, No. 1–2, Aug. 25, 2000, pp. 122–125, XP004227388 ISSN: 0022–328X.
Jafarpour, L., et al. "A sterically demanding nucleophilic carbene: 1,3–bis (2,6–diisopropylphenyl)imidazol–2–ylidene). Thermochemistry and catalytic application in olefin metathesis" *Journal of Organometallic Chemistry. Elsevier–Sequoia S.A. Lausanne, CH* vol. 606, No. 1, Jul. 14, 2000, pp. 49–54, XP004212112 ISSN: 0022–328X.
G. Maier: "2H–Imidazol–2–ylidene: New insights from a Matrix–Spectroscopic Study" *Chem EUR J*, vol. 5, No. 5, pp. 1590–1597 (1999) XP002172152.
Kuhn, N., et al., "Synthesis of imidazol–2–ylidenes by reduction of imidazole–2(3H)—thiones" *Synthesis, de, Georg Thieme Verlag. Stuttgart* No. 6, Jun. 1, 1993, pp. 561–562 XP002060701 ISSN: 0039–7881.
Arduengo, A. J., et al., "Electronic stabilization of nucleophilic carbenes" *Journal of the American Chemical Society, US, American Chemical Society, Washington DC* vol. 114, No. 4, Jul. 1, 1992 pp. 5530–5534 XP002032799 ISSN: 0002–7863.

* cited by examiner

*Primary Examiner*—Laura L. Stockton
(74) *Attorney, Agent, or Firm*—Drinker Biddle & Reath LLP

(57) ABSTRACT

The disclosure herein relates to imidazole carbenes and imidazole carbene salts. The disclosure also relates to the synthesis of imidazole carbenes and imidazole carbene salts. The imidazole carbenes disclosed include those synthesized by reacting an imidazole halide with a base under reduced pressure. The imidazole carbene salts disclosed include those synthesized by reaction of imidazole carbenes with an acid or alcohol suitable for creation of a salt. The disclosure also relates to the use of imidazole carbenes and imidazole carbene salts for the synthesis of organic liquids.

2 Claims, 1 Drawing Sheet

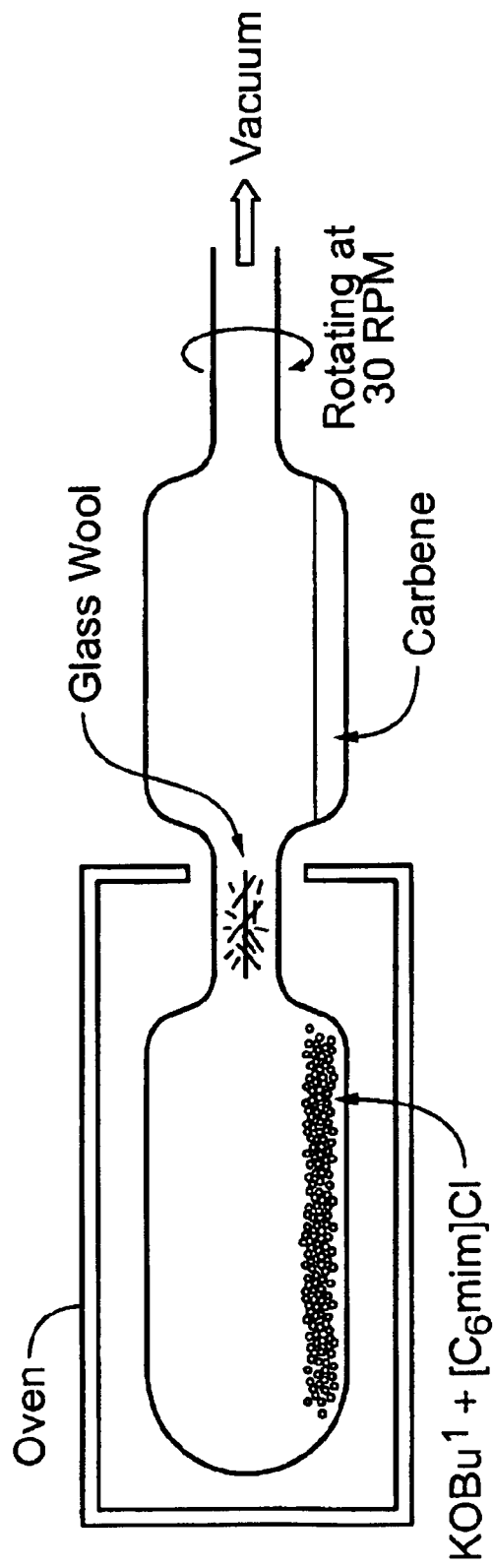

IMIDAZOLE CARBENES

This invention relates to a process for the synthesis of imidazole carbenes and the use thereof for the synthesis of ionic liquids.

BRIEF DESCRIPTION OF THE DRAWINGS

FIG. 1 shows the apparatus for the synthesis of imidazolium carbenes.

DETAILED DESCRIPTION

Carbenes are generally organic molecules which have a lone pair of electrons on a carbon atom and which in turn renders them highly reactive. As a result, carbenes are highly reactive intermediates in the synthesis of chemical compounds. Carbenes, due to their highly reactive nature, are generally only isolatable in the form of eg metal carbenoid species.

Numerous methods for the generation of imidazole carbenes have been reported. Starting from an imidazolium halide, the use of systems such as sodium hydride in ammonia or dimethyl sulfoxide (DMSO), sodium in ammonia, alkali metals in tetrahydrofuran (THF), metal t-butoxides in THF or DMSO, etc. These suffer from the disadvantage that very dry conditions and reagents have to be used, difficult separations under strictly anhydrous conditions are involved, and the reagents used can be expensive and inconvenient.

We have developed a simple procedure for the generation of the imidazolium carbene in 90–95% yield from an imidazolium chloride: this does not require solvents, filtrations, or lead to the production of noxious waste products.

According to the first aspect of the present invention, there is provided a process for the preparation of imidazolium carbenes of formula (I),

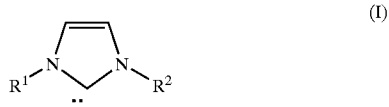
(I)

wherein $R_1$ and $R_2$, which can be the same or different, are hydrogen or linear or branched hydrocarbyl groups, comprising heating an imidazolium halide with a strong base under reduced pressure and separating the resultant products.

The process is preferably carried out under vacuum. The resultant products can be separated using any known separation techniques such as distillation.

The imidazolium halide may suitably be a chloride, bromide or an iodide and is preferably a chloride. $R_1$ and $R_2$ are suitably alkyl, alkaryl, aryl or aralkyl groups, more preferably alkyl groups. These hydrocarbyl groups suitably have from 1–20 carbon atoms, preferably from 1–8 carbon atoms. Specifically these substituents may be methyl or ethyl groups.

The strong base heated with the imidazolium halide may be any of the conventionally known strong bases such as eg alkali metal alkoxides, sodium hydride, sodium amide ($NaNH_2$) and the like. The strong base is suitably an alkali metal alkoxide in which the alkoxide group has 1–4 carbon atoms and may be a straight or branched chain. Specific examples of these are the methoxide, the ethoxide, the propoxide and the butoxide, especially the tertiary butoxide. Of the alkali metals in the alkoxide, potassium is preferred.

In one embodiment of the present invention, the process involves the distillation under vacuum of the carbene from a mixture of an imidazolium chloride and a commercially available metal alkoxide such as eg potassium t-butoxide The commercial metal alkoxide need not be further purified before use. The by-products of this reaction, where an imidazolium chloride is heated with potassium t-butoxide, are potassium chloride and t-butanol (which can be recycled). The method is straightforward, relatively cheap, and does not involve the production of noxious waste products.

Two examples of the reaction are shown below in which the substituents on the imidazolium groups are represented by the following abbreviations:

Et—Ethyl
Bu—Butyl
Me—Methyl
Bu$^t$—Tertiary butyl
KOBu$^t$—Potassium tertiary butoxide
HOBu$^t$—Tertiary butanol

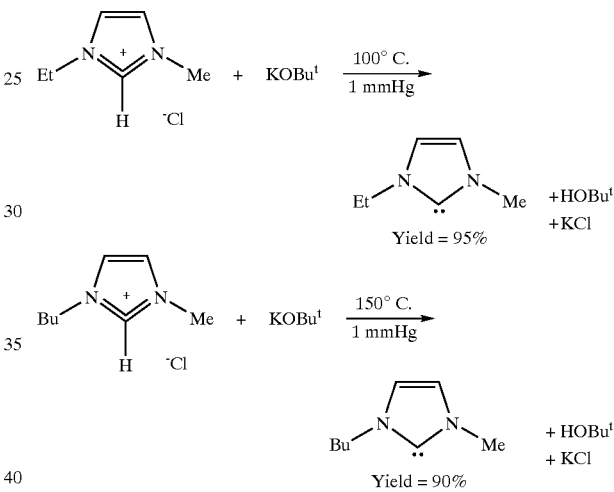

The two carbenes shown, which fume in moist air, are both colourless oils with a characteristic smell (freshly mown grass), of boiling point 90° C. and 130° C. at about 130 Pa (1 mm Hg) pressure, respectively. They appear to be thermally stable up to 200° C. for short periods of time, and stable at room temperature for several days (the mode of decomposition appears to be water-promoted disproportionation to a 2H-imidazoline and an oxidised species). However, they are extremely hygroscopic, reacting with moisture in the air to form the corresponding imidazolium hydroxide, itself being a novel ionic liquid. Consequently, they must be handled under dinitrogen or in an inert atmosphere glove box. The reaction of forming carbene itself is carried out in the substantial absence of any solvents. However, once produced, to facilitate handling of the carbenes, it may be dissolved in solvents. Suitable solvents for the dissolution of carbenes are limited, but aromatic, aliphatic (alkanes) and ether solvents appear to be appropriate. Halogenated and ketonic solvents must not be used, especially carbon tetrachloride, chloroform and primary alkyl halides, owing to a rapid exothermic transformation.

These carbenes can be used for conversion thereof to the corresponding imidazolium salts by a simple reaction with the acid form of the required anion. This reaction takes place according to the following equation;

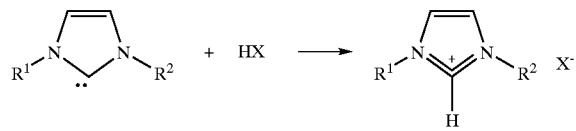

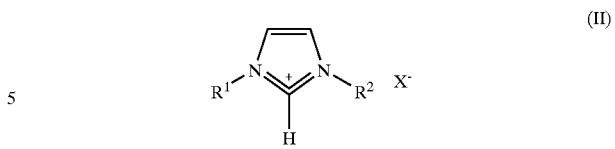

(II)

wherein $R^1$ and $R^2$ are as hereinbefore defined.

Thus, the present process can be used to generate imidazolium salts with a variety of anions such as those graphically represented in the equation below:

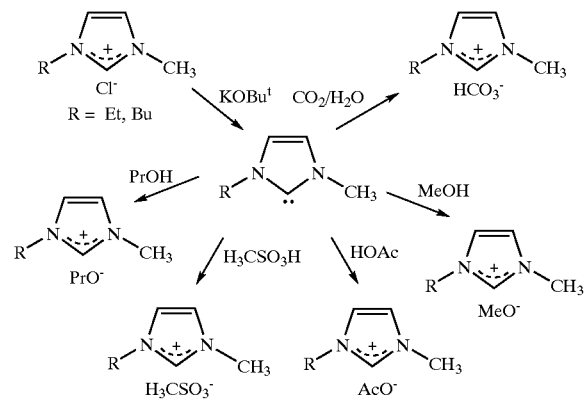

As can be seen from the above, the acid form of the anion can be any one of a vast variety of compounds including inter alia alcohols such as eg methanol or propanol, and acids such as eg carbonic acid, acetic acid or alkyl sulfonic acid.

Imidazolium salts of this type are essential components of many ionic liquids which are used as catalysts or solvents for catalysts in chemical reactions such as eg dimerisation, oligomerisation and polymerisation of olefins. Ionic liquids are primarily salts or mixtures of salts which melt below, at or above room temperature. Such salt mixtures include (alkyl) aluminium halides in combination with one or more of imidazolium halides, the latter being preferably substituted eg by alkyl groups. Examples of the substituted derivatives of the latter include one or more of 1-methyl-3-ethylimidazolium halide, 1-methyl-3-butylimidazolium halide, 1-ethyl-3-butylimidazolium halide and the like. These ionic liquids consist of a mixture where the mole ratio of the (alkyl) aluminium halide to the imidazolium halide is usually >1.0 but may be 1.0 or <1.0. Ionic liquids may also be simple binary salts, such as 1-methyl-3-butylimidazolium hexafluorophosphate, 1-methyl-3-ethylimidazolium acetate and 1-methyl-3-butylimidazolium nitrate.

The advantage of making the imidazolium salts by the present process, ie by reaction of two neutral molecules, is that it generates ionic liquids which are not contaminated by unwanted halide ions or metal ions. In addition to providing a novel and convenient route to known ionic liquids, it also permits the generation of novel ionic liquids, such as 1-methyl-3-alkylimidazolium alkoxides, 1-methyl-3-alkylimidazolium hydrogencarbonates and the corresponding imidazolium hydroxide which were hitherto unknown.

Thus according to a second aspect of the present invention, there is provided an imidazolium carbene of formula (I) as hereinbefore defined whenever prepared by the present invention.

According to a third aspect of the present invention, there is provided preparation of imidazolium salts of formula (II)

wherein $R_1$ and $R_2$, which can be the same or different, are hydrogen or linear or branched hydrocarbyl groups and $X^-$ is a cation,
comprising the reaction of an imidazolium carbene of formula (I) as hereinbefore defined with an acid or alcohol.

According to a fourth aspect of the present invention, there is provided an imidazolium salt of formula (II) as hereinbefore defined whenever prepared by the present invention.

According to a fifth aspect of the present invention, there is provided use of an imidazolium salt of formula (II) as hereinbefore defined as an ionic liquid.

The present invention is further illustrated with reference to FIG. 1 and the following Examples:

EXAMPLES

1. Preparation of Carbenes 1.1 1-Ethyl-3-methylimidazol-2-ylidine

All manipulations were performed under a stream of dry dinitrogen or in a glove box. In a round-bottomed flask (50 cm$^3$), 1-ethyl-3-methyl imidazolium chloride (8.7 g, 50 mmol) and a commercial sample of potassium t-butoxide (7.7 g, 75 mmol, unpurified, 95% ex Aldrich) were heated in a Kugelrohr apparatus at 125° C. at about 130 Pa (1 mm Hg) pressure for 1 h. A colourless oil was collected and transferred to a clean round-bottomed flask (50 cm$^3$). This was redistilled on the Kugelrohr apparatus to give 5.3 g of a colourless oil. NMR analysis showed this oil to be 1-ethyl-3-methylimidazol-2-ylidine (95% yield). The product has a tendency to rapidly turn orange on contact with the air. The carbene produced by this Example was characterised using $^1$H and $^{13}$C NMR spectroscopy and the following peaks were identified:

| $^1$H NMR | 7.21 | 1H | singlet | $^{13}$C NMR | 208.5 | C |
|---|---|---|---|---|---|---|
| | 7.08 | 1H | singlet | | 117.5 | CH |
| | 4.03 | 2H | quartet | | 116.2 | CH |
| | 3.73 | 3H | singlet | | 42.5 | CH$_2$ |
| | 1.38 | 3H | triplet | | 34.7 | CH$_3$ |
| | | | | | 14.6 | CH$_3$ |

1.2 1-Butyl-3-methylimidazol-2-ylidine

The same procedure as in Section 1.1 above was used for making the analogous butyl carbene except that the reaction temperature and distillation temperature were slightly (ca. 30° C.) higher.

The carbene produced by this Examples was characterised using $^1$H and $^{13}$C NMR spectroscopy and the following peaks were identified:

| $^1$H NMR | 7.16 | 1H | singlet | $^{13}$C NMR | 210.2 | C |
|---|---|---|---|---|---|---|
| | 7.02 | 1H | singlet | | 117.5 | CH |
| | 4.02 | 2H | quartet | | 116.7 | CH |
| | 3.68 | 3H | singlet | | 47.4 | CH$_2$ |
| | 1.78 | 2H | pentet | | 34.6 | CH$_3$ |
| | 1.38 | 2H | hextet | | 31.3 | CH$_2$ |

-continued

| | | | | | |
|---|---|---|---|---|---|
| 0.90 | 3H | triplet | | 17.1 | CH$_2$ |
| | | | | 10.9 | CH$_3$ |

2. Preparation of Imidazolium Salts:

The method depends upon the careful mixing of a stoichiometric amount of carbene with an acid or alcohol, or, alternatively, excess acid, if the excess acid is readily separable (eg carbonic acid).

2.1 1-Butyl-3-methylimidazolium hydrogencarbonate:

A mixture of 1-butyl-3-methylimidazolium chloride (4.37 g, 25 mmol) and potassium t-butoxide (3.95 g, 35 mmol) was placed in a 50 cm³ round bottomed flask in a glove box. The flask was transferred to a Kugelrohr apparatus and the mixture was heated at 150° C., at about 130 Pa (1 mm Hg) pressure. A colourless oil (1-butyl-3-methylimidazol-2-ylidine) was collected. The reaction was adjudged to be complete after 30 minutes and the oil was immediately poured into a 500 cm³ round bottom flask containing de-ionised water (100 cm³) and dry ice (ca. 10 g). The flask was agitated until the dry ice had evaporated and the water was evaporated on a rotary evaporator. Toluene (3×50 cm³) was added to the flask and removed on a rotary evaporator (this procedure was used to azeotropically remove water from the ionic liquid) and finally, the resultant viscous brown oil was heated to 50° C. at 133.4 Pa (1 mm Hg) for 2 hours. Weight of product=3.51 g, yield=70%. The same NMR spectroscopy as used previously to characterise the carbene was used to characterise the imidazolium salts. The results were as follows:

| $^1$H NMR | 8.85 | 1H | singlet | | $^{13}$C NMR | 159.0 | C(HCO$_3$) |
|---|---|---|---|---|---|---|---|
| | 7.61 | 1H | singlet | | | 135.7 | CH |
| | 7.57 | 1H | singlet | | | 122.0 | CH |
| | 4.99 | | singlet | (HOD) | | 120.6 | CH |
| | 4.31 | 2H | triplet | | | 47.7 | CH$_2$ |
| | 4.02 | 3H | singlet | | | 34.1 | CH$_3$ |
| | 1.95 | 2H | hextet | | | 29.7 | CH$_2$ |
| | 1.42 | 2H | pentet | | | 17.2 | CR$_2$ |
| | 1.03 | 3H | triplet | | | 11.2 | CH$_3$ |
| Solvent = D$_2$O | | | | | | | |
| IR (NaCl plate): ν = 1666 cm$^{-1}$ | | | | C=O | | | |
| ν = 3600–2350 cm$^{-1}$ | | | | O—H | | | |
| Empirical solubilities: | | | | | | | |
| Soluble: | | | water, methanol, ethanol | | | | |
| Partially soluble: | | | acetone | | | | |
| Insoluble: | | | ethyl acetate, diethyl ether | | | | |

2.2 1-Ethyl-3-methylimidazolium methoxide:

A mixture of 1-ethyl-3-methyl imidazolium chloride (3.66 g, 25 mmol) and potassium t-butoxide (3.96 g, 35 mmol) was placed in a 50 cm³ round bottomed flask in a glove box. The flask was transferred to a Kugelrohr apparatus and the mixture was heated at 140° C., at about 130 Pa (1 mm Hg) pressure. A colourless oil (1-ethyl-3-methylimidazol-2-ylidine) was collected. The reaction was adjudged to be complete after 30 minutes and the apparatus was pressurised with dry nitrogen. Anhydrous methanol (1.0 cm³, 27 mmol) was added to the carbene by syringe. Excess methanol was removed by reconnecting to the vacuum line (1 mm Hg) and rotating the reaction vessel for 1 hour. The NMR spectra were recorded neat, using an acetone-d$^6$ external lock. Yield estimated at 85–90% (based on NMR).

| $^1$H NMR | 8.99 | 1H | singlet (broad) | $^{13}$C NMR | 190.2 | CH (broad) |
|---|---|---|---|---|---|---|
| | 7.56 | 1H | singlet | | 118.4 | CH |
| | 7.45 | 1H | singlet | | 116.4 | CH |
| | 4.38 | 2H | quartet | | 45.1 | CH$_2$ |
| | 4.02 | 3H | singlet | | 42.3 | CH$_3$ |
| | 3.66 | 3H | singlet | | 34.0 | CH$_3$ |
| | 1.63 | 3H | triplet | | 14.0 | CH$_3$ |

Note: The product is extremely hygroscopic and decomposes slowly at room temperature. This decomposition appears to be water catalysed.

2.3 1-Butyl-3-methylimidazolium propoxide:

1-Butyl-3-methylimidazol-2-ylidine (2.00 g, 16.1 mmol) was prepared as in Section 2.1 above. This was cautiously added to n-propanol (0.97 g, 16.1 mmol) by pipette in a glove box. The NMR spectra were recorded neat, using an acetone-d$^6$ external lock. Yield estimated at 95% (based on NMR).

| $^1$H NMR | 8.92 | 1H | singlet (broad) | $^{13}$C NMR | 190.1 | CH (broad) |
|---|---|---|---|---|---|---|
| | 7.46 | 1H | singlet | | 118.2 | CH |
| | 7.41 | 1H | singlet | | 117.3 | CH |
| | 4.33 | 2H | triplet | | 59.8 | CH$_2$ |
| | 4.02 | 3H | singlet | | 47.2 | CH$_2$ |
| | 3.86 | 2H | triplet | | 34.0 | CH$_3$ |
| | 2.10 | 2H | pentet | | 30.9 | CH$_3$ |
| | 1.86 | 2H | hexet | | 29.0 | CH$_2$ |
| | 1.60 | 2H | hexet | | 24.3 | CH$_2$ |
| | 1.20 | 3H | triplet | | 10.8 | CH$_3$ |
| | 1.19 | 3H | triplet | | 8.0 | CH$_3$ |

Note: The product is extremely hygroscopic and decomposes very slowly at room temperature. This decomposition appears to be water catalysed. It appears to be significantly more stable than 1-ethyl-3-methylimidazolium methoxide.

2.4 1-Butyl-3-methylimidazolium acetate:

1-Butyl-3-methylimidazol-2-ylidine (2.00 g, 16.1 mmol) was prepared as in Section 2.1 above. This was cautiously added to glacial acetic acid (0.97 g, 16.1 mmol) by pipette in a glove box over a 15 minute period. The NMR spectra were recorded neat, using an acetone-d$^6$ external lock. Yield estimated at 95% (based on NMR).

| $^1$H NMR | 10.61 | 1H | singlet | $^{13}$C NMR | 172.1 | C |
|---|---|---|---|---|---|---|
| | 8.45 | 1H | singlet | | 136.3 | CH |
| | 8.32 | 1H | singlet | | 121.6 | CH |
| | 4.31 | 2H | triplet | | 120.5 | CH |
| | 4.02 | 3H | singlet | | 46.0 | CH$_2$ |
| | 1.72 | 2H | pentet | | 32.8 | CH$_3$ |
| | 1.70 | 3H | singet | | 29.6 | CH$_2$ |
| | 1.15 | 2H | hexet | | 28.6 | CH$_3$ |
| | 0.72 | 3H | triplet | | 22.2 | CH$_2$ |
| | | | | | 10.4 | CH$_3$ |

The following are further non-limiting examples;
1-hexyl-3-methylimidazolylidine.

1-hexyl-3-methylimidazolium chloride (10.0 g) was placed in a 100 cm³ Kugelrohr flask and connected to a Kugelrohr apparatus (FIGS. 1,2). This was heated at 100° C. for 1 hour at 1 mmHg pressure, then cooled to room temperature. The flask was transferred to a dry glove box and potassium tert-butoxide (10.0 g) was added to the 1-hexyl-3-methylimidazolium chloride. The apparatus was reassembled and heated at 160° C. for 2 hours. During this period, 1-hexyl-3-methylimidazolylidine distilled into the receiving flask and the tert-butanol condensed into a liquid nitrogen trap connected to the vacuum pump. The orange coloured 1-hexyl-3-methylimidazolylidine was analysed by $^1$H and $^{13}$C NMR spectroscopy. The crude product was redistilled in the Kugelrohr apparatus (bp=160° C. at 1 mmHg) to give an extremely moisture sensitive colorless oil (6.5 g, 79%); δH (300 MHz, neat, external TMS reference) 6.97 (1H, s), 6.92 (1H, s), 3.94 (2H, q, J=7.3 Hz), 3.62 (3H, s), 1.72 (2H, m), 1.26 (6H, m), 0.85 (3H, t, J=7.3 Hz); $^{13}$C NMR δC (75 MHz, neat, external TMS reference) 209.6 (C), 119.6 (CH), 118.5 (CH), 49.9 (CH$_2$), 35.7 (CH$_3$), 31.5 (CH$_2$), 31.3 (CH$_2$), 31.1 (CH$_2$), 22.1 (CH$_2$), 13.4 (CH$_3$).

1-Hexyl-3-methylimidazolium Hydrogen Carbonate

Solid carbon dioxide (dry ice) (ca. 25 g) was added to distilled water (100 g), with stirring from a magnetic stirring flea in a 500 cm$^3$ beaker, in a fume hood. 1-hexyl-3-methylimidazolylidine (6.0 g, 36.1 mmol) was added to the water and carbon dioxide mixture. The mixture was allowed to warm to room temperature, and was washed with dichloromethane (3×25 cm$^3$). The water was evaporated on a rotary evaporator (making sure the temperature did not exceed 60° C.) and the 1-hexyl-3-methylimidazolium hydrogen carbonate was dried under vacuum (1 mmHg) for 4 hours at 60° C. This gave 7.8 g (94%) of a straw coloured viscous liquid. δH (300 MHz, D$_2$O, TMS reference) 8.28 (1H, s, D$_2$O exchangable) 7.43 (1H, s), 7.33 (1H, s), 4.78 (1H, s), 4.04 (2H, q, J=7.3 Hz), 3.77 (3H, s), 1.73 (2H, m), 1.32 (6H, m), 0.71 (3H, t, J=7.3 Hz); $^{13}$C NMR δC (75 MHz, D$_2$O, TMS reference) 161.3 (C), 135.8 (CH, D$_2$O exchangeable), 123.8 (CH), 122.5 (CH), 49.8 (CH$_2$), 35.9 (CH$_3$), 30.6 (CH$_2$), 29.5 (CH$_2$), 25.3 (CH$_2$), 22.1 (CH$_2$), 13.6 (CH$_3$).

This salt could be converted to other 1-hexyl-3-methylimidazolium salts (or ionic liquids) by reaction with the acid form of the desired anion in water, followed by evaporation of the water.

1-Octyl-3-methylimidazolylidine.

1-Octyl-3-methylimidazolium chloride (5.0 g, 21.7 mmol) was placed in a 50 cm$^3$ Kugelrohr flask and connected to a Kugelrohr apparatus (FIG. 1). This was heated at 100° C. for 1 hour at 1 mmHg pressure, then cooled to room temperature. The flask was transferred to a dry glove box and potassium tert-butoxide (5.0 g, excess) was added to the 1-octyl-3-methylimidazolium chloride. The apparatus was reassembled and heated at 200° C. for 1 hour. During this period, 1-octyl-3-methylimidazolylidine distilled into the receiving flask and the tert-butanol condensed into a liquid nitrogen trap connected to the vacuum pump. The crude product was redistilled in the Kugelrohr apparatus (bp= 190–200° C. at 1 mmHg) to give an extremely moisture sensitive oil (2.87 g, 68%). The yellow coloured 1-octyl-3-methylimidazolylidine solidified on standing was immediately used in further reactions.

1-Octyl-3-methylimidazolium acetate

1-Octyl-3-methylimidazol-2-ylidine (2.00 g, 16.1 mmol) prepared above, was cautiously added to glacial acetic acid (0.97 g, 16.1 mmol) by pipette in a glove box over a 15 minute period with stirring from a magnetic stirrer flea. The ionic liquid formed was used unpurified. NMR data: δH (300 MHz, neat, external TMS reference) 10.61 (1H, s), 8.45 (1H, s), 8.32 (1H, s), 4.31 (3H, t), 4.02, (3H, s), 1.72 (2H, m), 1.70 (2H, s), 1.15 (10H, m), 0.72 (3H, t, J=7.2 Hz); $^{13}$C NMR δC (75 MHz, neat, external TMS reference) 172.1 (C), 136.3 (CH), 121.6 (CH), 120.5 (CH), 46.0 (CH$_2$), 32.8 (CH$_3$), 29.6 (5×CH$_2$), 28.6 (CH$_3$), 22.2 (CH$_2$), 10.4 (CH$_2$).

What is claimed is:
1. 1-Methyl-3-alkylimidazolium alkoxide.
2. 1-Methyl-3-alkylimidazolium hydrogencarbonate.

* * * * *